US011103175B2

(12) United States Patent
Albert et al.

(10) Patent No.: US 11,103,175 B2
(45) Date of Patent: *Aug. 31, 2021

(54) MOBILE ECG SENSOR APPARATUS

(71) Applicant: AliveCor, Inc.

(72) Inventors: David E. Albert, Oklahoma City, OK (US); Simon Prakash, Los Gatos, CA (US); Bruce Satchwell, Gold Coast (AU); Jonathan Beck, Mountain View, CA (US)

(73) Assignee: AliveCor, Inc., Mountain View, CA (US)

( * ) Notice: Subject to any disclaimer, the term of this patent is extended or adjusted under 35 U.S.C. 154(b) by 50 days.

This patent is subject to a terminal disclaimer.

(21) Appl. No.: 16/440,738

(22) Filed: Jun. 13, 2019

(65) Prior Publication Data

US 2019/0380609 A1  Dec. 19, 2019

Related U.S. Application Data

(60) Continuation of application No. 15/923,699, filed on Mar. 16, 2018, now Pat. No. 10,342,444, which is a continuation-in-part of application No. 15/721,038, filed on Sep. 29, 2017, now Pat. No. 9,986,925, which is a continuation of application No. 15/140,072, filed on Apr. 27, 2016, now Pat. No. 9,833,158, which is a continuation of application No. 14/254,310, filed on Apr. 16, 2014, now Pat. No. 9,351,654, which is a continuation-in-part of application No. 13/108,738, filed on May 16, 2011, now abandoned, which is a continuation-in-part of application No. 12/796,188, filed on Jun. 8, 2010, now Pat. No. 8,509,882, application No. 16/440,738, which is a continuation of application No. 15/923,699, filed on Mar. 16, 2018, now Pat. No. 10,342,444, which is a continuation-in-part of application No. 15/486,777, filed on Apr. 13, 2017, which is a continuation of application No. 13/964,490, filed on Aug. 12, 2013, (Continued)

(51) Int. Cl.
| | |
|---|---|
| A61B 5/00 | (2006.01) |
| A61B 5/316 | (2021.01) |
| G06Q 50/22 | (2018.01) |
| A61B 5/0245 | (2006.01) |
| A61B 5/25 | (2021.01) |
| A61B 5/327 | (2021.01) |
| A61B 5/332 | (2021.01) |
| A61B 5/333 | (2021.01) |
| A61B 5/339 | (2021.01) |
| A61B 5/349 | (2021.01) |
| A61B 5/0205 | (2006.01) |

(52) U.S. Cl.
CPC ............. *A61B 5/316* (2021.01); *A61B 5/002* (2013.01); *A61B 5/0006* (2013.01); *A61B 5/0015* (2013.01); *A61B 5/0022* (2013.01); *A61B 5/0245* (2013.01); *A61B 5/25* (2021.01); *A61B 5/327* (2021.01); *A61B 5/332* (2021.01); *A61B 5/333* (2021.01); *A61B 5/339* (2021.01); *A61B 5/349* (2021.01); *A61B 5/6898* (2013.01); *A61B 5/7225* (2013.01); *G06Q 50/22* (2013.01); *A61B 5/0205* (2013.01); *A61B 5/7257* (2013.01); *A61B 2560/0412* (2013.01)

(58) Field of Classification Search
CPC ........................... A61B 5/0404; A61B 5/0006
USPC ......................................... 600/509, 323, 309
See application file for complete search history.

*Primary Examiner* — Nadia A Mahmood
(74) *Attorney, Agent, or Firm* — Womble Bond Dickinson (US) LLP

(57) ABSTRACT

Disclosed systems include mobile ECG sensors, systems and methods. Some embodiments provide ECG sensors in a credit card form factor that allows a user to contact two electrically isolated electrodes to measure heart electrical signals for a Lead 1 ECG.

13 Claims, 14 Drawing Sheets

Related U.S. Application Data now Pat. No. 9,649,042, which is a division of application No. 12/796,188, filed on Jun. 8, 2010, now Pat. No. 8,509,882.

MOBILE ECG SENSOR APPARATUS

CROSS-REFERENCE TO RELATED APPLICATIONS

This application is a continuation of U.S. patent application Ser. No. 15/923,699, filed Mar. 16, 2018, which is a continuation-in-part of U.S. patent application Ser. No. 15/721,038, filed Sep. 29, 2017, now U.S. Pat. No. 9,986,925, which is a continuation of U.S. patent application Ser. No. 15/140,072, filed Apr. 27, 2016, now U.S. Pat. No. 9,833,158, which is a continuation of U.S. patent application Ser. No. 14/254,310, filed Apr. 16, 2014, now U.S. Pat. No. 9,351,654, which is a continuation-in-part of U.S. patent application Ser. No. 13/108,738, filed May 16, 2011, which is a continuation-in-part of U.S. patent application Ser. No. 12/796,188, filed Jun. 8, 2010, now U.S. Pat. No. 8,509,882.

This application is also a continuation of U.S. patent application Ser. No. 15/923,699, filed Mar. 16, 2018, which is a continuation-in-part of U.S. patent application Ser. No. 15/486,777, filed Apr. 13, 2017, now Publication US-2017-0215755, which is a continuation of U.S. patent application Ser. No. 13/964,490, filed Aug. 12, 2013, now U.S. Pat. No. 9,649,042, which is a divisional of U.S. patent application Ser. No. 12/796,188, filed Jun. 8, 2010, now U.S. Pat. No. 8,509,882, each of which is incorporated herein by reference in its entirety.

INCORPORATION BY REFERENCE

All publications and patent applications mentioned in this specification are herein incorporated by reference to the same extent as if each individual publication or patent application was specifically and individually indicated to be Incorporated by reference.

BACKGROUND

1. Field of Invention

The presently claimed and disclosed inventive concept(s) relates generally to personal physiology monitoring devices and methods and more particularly, but not by way of limitation, to devices, systems and software for providing ECG, heart rate and cardiac arrhythmia monitoring utilizing a computing device such as a smartphone.

2. Background of the Invention

The prior art includes numerous systems wherein ECG data or the like is monitored and or transmitted from a patient to a particular doctor's office or health service center. For example. U.S. Pat. No. 5,735,285 discloses use of a handheld device that converts a patient's ECG signal into a frequency modulated audio signal that may then be analyzed by audio inputting via a telephone system to a selected hand-held computer device or to a designated doctor's office. Similarly, U.S. Pat. No. 6,264,614 discloses a heart monitor, which is manipulated by the patient to sense a biological function such as a heart beat, and outputs an audible signal to a computer microphone. The computer processes the audible signal and sends resulting data signals over a network or Internet. U.S. Pat. No. 6,085,633 discloses a heart monitor that a patient can hold against his or her chest. The device outputs an audible signal responsive to the function or condition, such as the beating of the heart, to a microphone connected to a computer. Each of these audio transmissions is limited to transmission of audible sound. In other words, frequency modulated sound transmission at carrier frequencies above that heard by humans, i.e. above 17 kHz, was not contemplated.

U.S. Pat. App. Publication No. 2004/0220487 discloses a system with ECG electrodes which sense ECG electrical signals which are combined and amplitude modulated. The composite signal is transmitted via wire or wirelessly to the sound port in a computing device. A digital band pass filter having a pass band from 10 kHz to 21 kHz is considered; however, there is no consideration of demodulation means at this frequency range using commercially available computing devices. Additionally, the use of sound waves to effect transmission is not contemplated.

U.S. Pat. App. Publication No. 2010/0113950 discloses an electronic device having a heart sensor including several leads for detecting a user's cardiac signals. The leads are coupled to interior surfaces of the electronic device housing to hide the sensor from view. Using the detected signals, the electronic device can then identify or authenticate the user.

U.S. Pat. No. 6,820,057 discloses a system to acquire, record, and transmit ECG data wherein the ECG signals are encoded in a frequency modulated audio tone having a carrier tone in the audio range. However, there is no real consideration of carrier frequencies above about 3 kHz, no consideration of carrier frequencies above the audible, and no consideration of demodulation methods at higher carrier frequencies.

Limitations of the prior art utilizing transtelephonic and audible acoustic signals include a signal to noise ratio that is diminished by talking or any other noisy activity in the vicinity, thus potentially jeopardizing the integrity of the heart monitoring data signals. Additionally, the audible signals can be heard by anyone in the vicinity of the computer and heart monitor, which can be bothersome to the user as well as to others in the vicinity. Other applications fail to provide a reliable, inexpensive personal monitoring device that is readily compatible with existing computing devices such as smartphones. It would be advantageous if these issues were addressed in a personal monitoring device transmitting real time physiological data.

DETAILED DESCRIPTION

Before explaining at least one embodiment of the invention in detail, it is to be understood that the invention is not limited in its application to the details of construction, experiments, exemplary data, and/or the arrangement of the components set forth in the following description. The invention is capable of other embodiments or of being practiced or carried out in various ways. Also, it is to be understood that the terminology employed herein is for purpose of description and should not be regarded as limiting.

In the following detailed description of embodiments of the disclosure, numerous specific details are set forth in order to provide a more thorough understanding of the disclosure. However, it will be apparent to one of ordinary skill in the art that the concepts within the disclosure can be practiced without these specific details. In other instances, well-known features have not been described in detail to avoid unnecessarily complicating the description.

Figure 1:
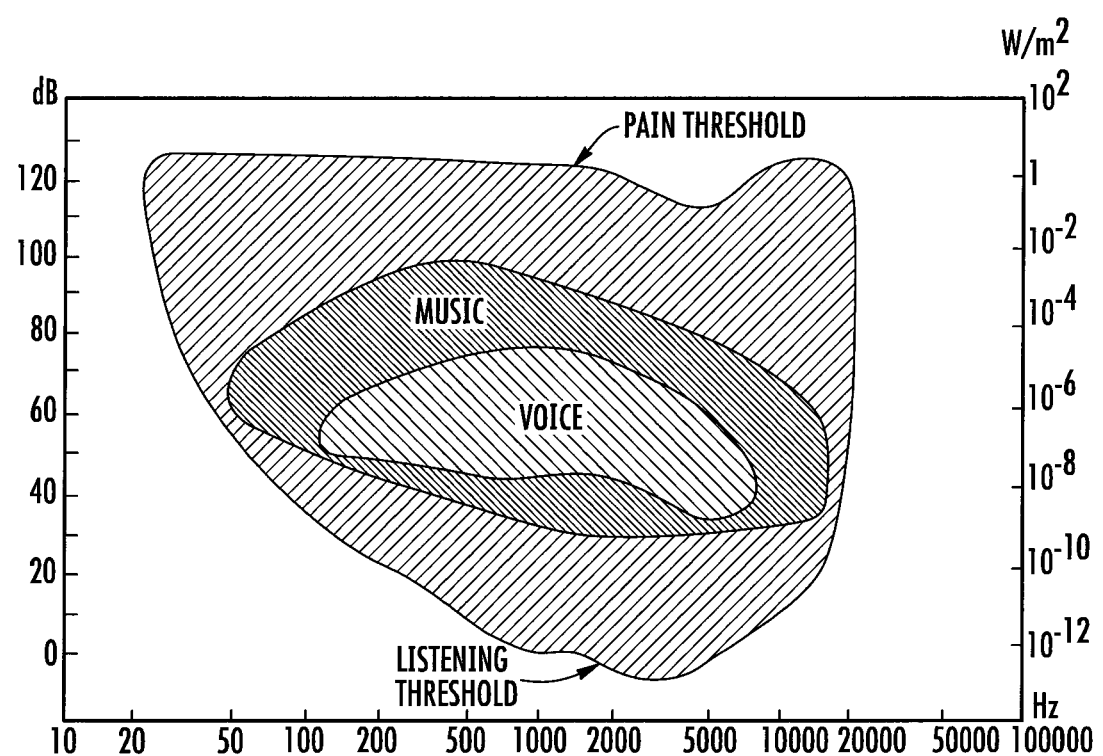
FIG. 1 is a pictorial representation of the human range and thresholds of hearing from http://en.labs.wikimedia.org/wiki/Acoustics.
Figure 2:
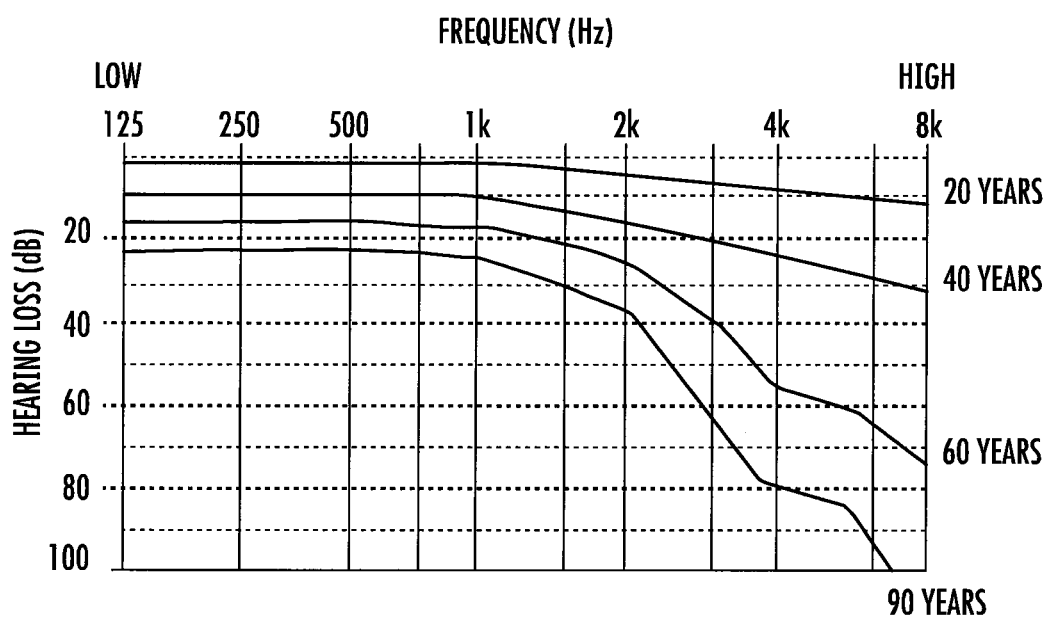
FIG. 2 is a pictorial representation of hearing loss with age from www.neuroreille.com/promenade/english/audiometry/audiometry.htm.

The human hearing range is often referred to as 20 Hz to 20 kHz. A maximum aural range in children, under ideal laboratory conditions, is actually as low as 12 Hz and as high as 20 kHz. However, as shown in FIG. 1, the threshold frequency, i.e. the minimum intensity detectable, rises rapidly to the pain threshold between 10 kHz to 20 kHz. Thus, sounds above about 16 kHz must be fairly intense to be heard. Almost immediately from birth, the threshold sound level for these higher frequencies increases. As shown in FIG. 2, an average 20 year old has lost about 10 dB in the 8 kHz range, while at age 90, the average person has lost over 100 dB at this frequency.

An example product using very high frequency sound is the Mosquito alarm, a controversial device emitting an intentionally annoying 17.4 kHz alarm and used to discourage younger people from loitering. Due to adult hearing loss at this frequency, it is typically heard only by people less than 25 years of age. Similarly, students make use of the adult hearing loss by using "mosquito" ringtones in the 15-17 kHz on their cell phones during school. The students can hear the "mosquito" ringtones while their adult teachers cannot. The term "ultrasonic" typically means above the range perceived by humans. However, as demonstrated, the upper limit of hearing frequency varies with individuals and with age generally. Because of the differences in this upper limit, the term "ultrasonic" is defined herein and in the appending claims to refer to "sound frequencies of 17 kHz or greater."

Figure 3:
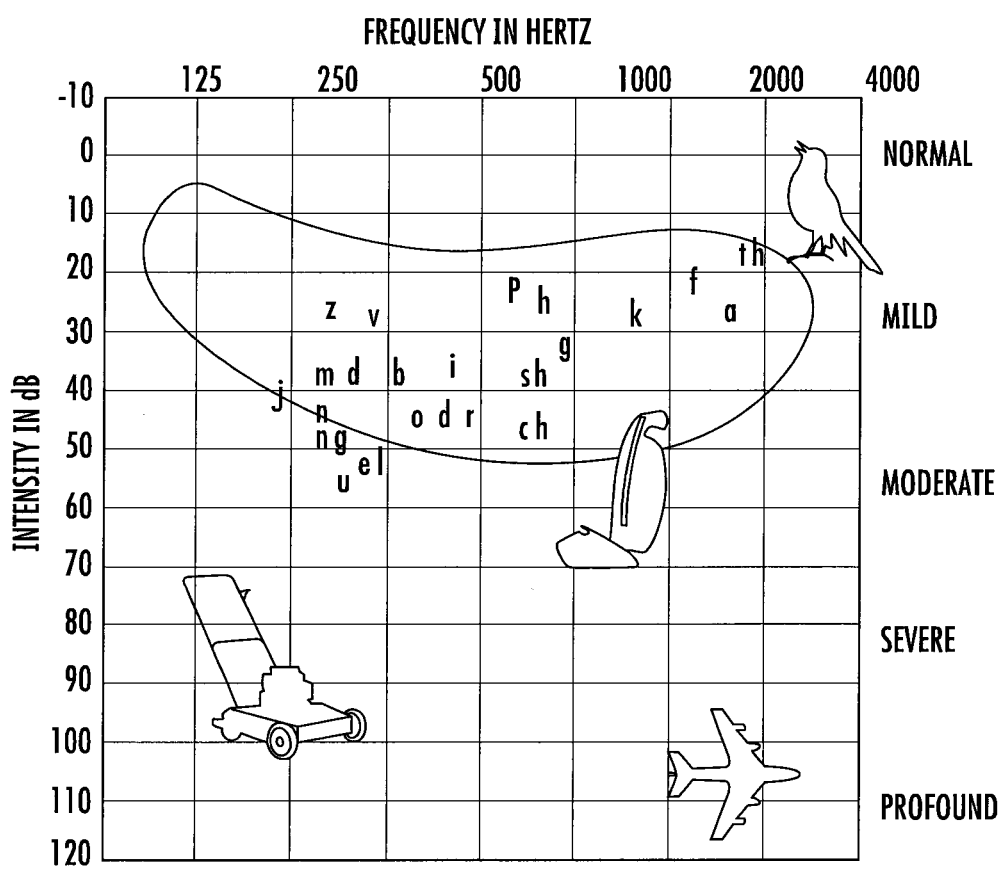
FIG. 3 is an audiogram illustrating the intensity and frequency of common sounds from www.hearinglossky.org/hlasurvival1.html.

Interestingly, however, there is very little ambient sound or noise above about 10 kHz. Referring to FIG. 3, most everyday sounds occur at frequencies below about 4 kHz. Thus, use of signals in the ultrasonic range is not only silent to those around, but also provides a very desirable signal to noise ratio (SNR).

Acoustic engineers safely assume that any frequency above about 20 kHz will have no effect on the perceived sound and they filter everything above this range. Sounds below 20 kHz but still in the ultrasonic range are of little concern, and standard sampling procedures have been established accordingly. It is generally understood that sampling an analog signal, whether a radio signal or audible sound signal, requires a sampling frequency $f_s$ such that $f_s/2 > f$, wherein f is the sinusoid frequency. For this reason, sound systems are designed to sample the sound at the now standard sample rate of 44.1 kHz, set somewhat higher than the calculated Nyquist-Shannon sampling rate of 40 kHz for a 20 kHz sound upper limit. Actual demodulation of an FM narrow band signal in the ultrasonic range, using existing demodulation procedures, computers, telephones, cell phones, stereo sound systems, etc., would result in very poor reproduction of the original signal. This is unfortunate because, as discussed above, a carrier signal in the ultrasonic range would also have a very low signal to noise ratio due to the fact that there is very little natural "noise" at these higher frequencies.

The inventive concept(s) disclosed herein is directed to a personal monitoring device, methods and systems for measuring physiological signals and transmitting those measurements wirelessly and soundlessly using frequency modulated ultrasonic signals having a much improved signal to noise ratio compared to traditional transtelephonic methods. Also provided are methods and algorithms to receive and demodulate the ultrasonic signals with excellent accuracy using existing computer and smart phone technology.

Figure 4:
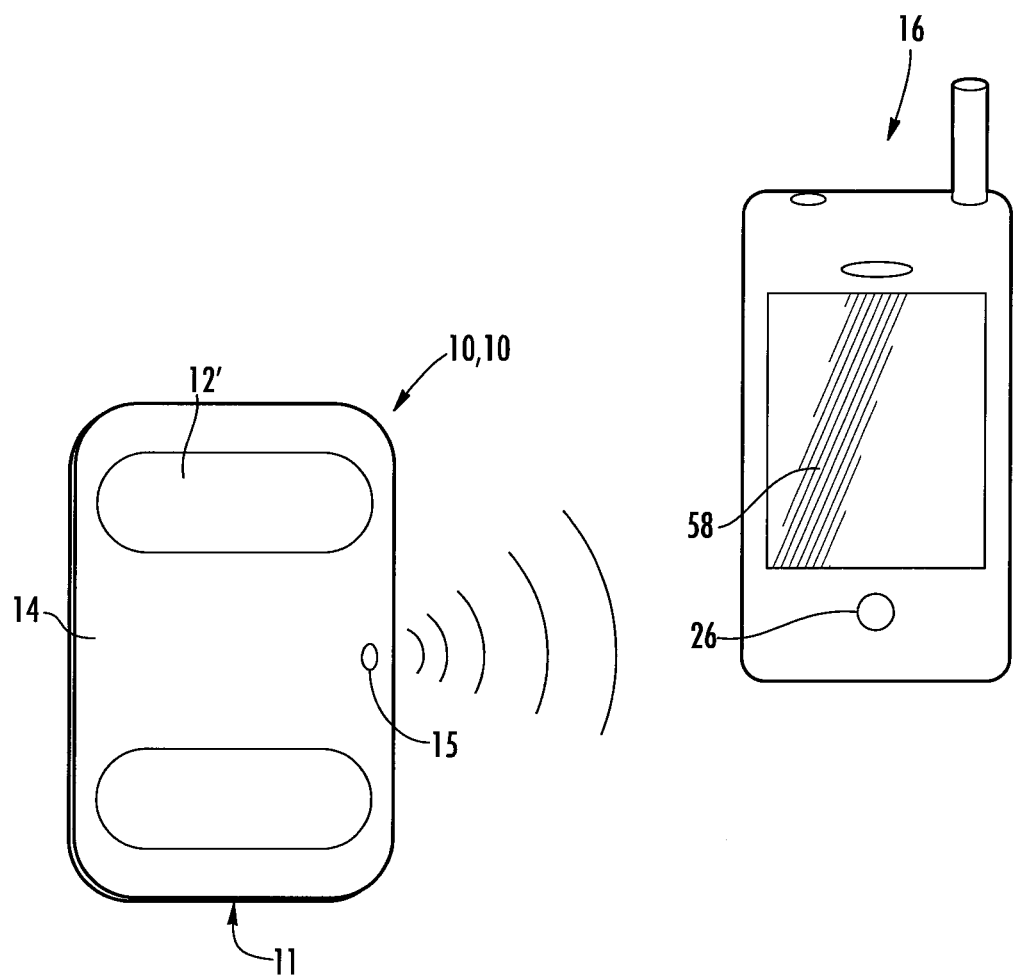
FIG. 4 is a schematic representation of an embodiment of a personal monitoring device transmitting to a computing device.
Figure 5:
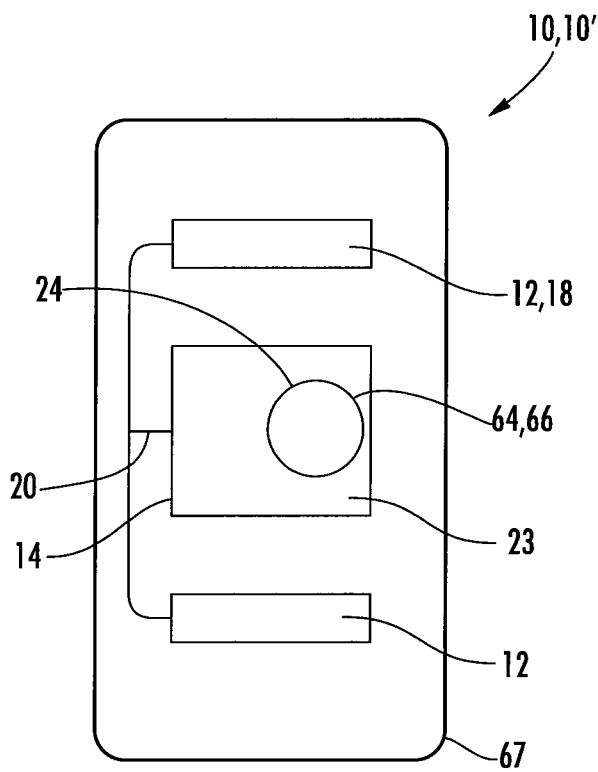
FIG. 5 is a schematic representation of another embodiment of a personal monitoring device of the present invention.

The presently claimed and disclosed inventive concepts provide a personal monitoring device 10, embodiments of which are shown schematically in FIG. 4 and FIG. 5. The acquisition electronics 11 of the monitoring device 10 includes a sensor assembly 12 configured to sense physiological signals upon contact with a user's skin. The sensor assembly 12 produces electrical signals representing the sensed physiological signals, which input to a converter assembly 14, integrated with the sensor assembly 12. Converter assembly 14 converts the electrical signals generated by the sensor assembly 12 to a frequency modulated ultrasonic signal which is output by ultrasonic transmitter 24. In one embodiment, the frequency modulated ultrasonic signal has a carrier frequency in the range of from about 18 kHz to about 24 kHz. In another embodiment, the frequency modulated ultrasonic signal has a carrier frequency in the range of from about 20 kHz to about 24 kHz.

The sensor assembly 12 can include any suitable sensor operative to detect a physiological signal that a user desires to monitor. Nonlimiting examples of such physiological signals include, but are not limited to, respiration, heart beat, heart rate, electrocardiogram (ECG), electromyogram (EMG), electrooculogram (EOG), pulse oximetry, photoplethysmogram (PPG) and electroencephalogram (EEG).

Figure 6:
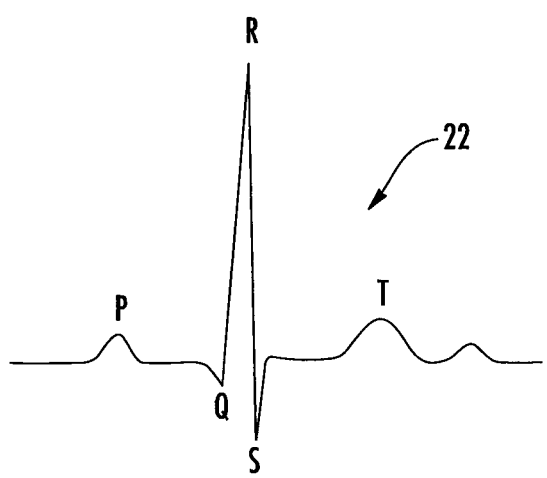
FIG. 6 is an example of graphical ECG representation.

A respiration detector can be a conventional microphone assisted stethoscope 12'. Mean beat and heart rate can be detected as well using a conventional microphone assisted stethoscope 12', or by using an electrode assembly 18 to sense electrical signals generated by the heart over time. Such electrodes 18 can also be used to detect the electrical activity of the heart over time for electrocardiography (ECG). An ECG is a measurement of the small electrical changes on the skin generated when the heart muscle depolarizes during each heart beat. The output from a pair of electrodes 18 is known as a lead 20. Small rises and falls in the voltage between two electrodes placed on either side of the heart can be processed to produce a graphical ECG representation 22 such as the example ECG shown in FIG. 6.

Electromyography (EMG) detects the electrical potential generated by muscle cells when the cells are electrically or neurologically activated. The signals can be analyzed to detect medical abnormalities. Electrooculography (EOG) is a technique for measuring the resting potential of the retina. Usually, pairs of electrodes 18 are placed either above and below the eye, or to the left and right of the eye, and a potential difference measurement is a measure for the eye position.

The oxygenation of a person's hemoglobin can be monitored indirectly in a noninvasive manner using a pulse oximetry sensor, rather than measuring directly from a blood sample. The sensor is placed on a thin part of the person's body, such as a fingertip or earlobe, and a light containing both red and infrared wavelengths is passed from one side to the other. The change in absorbance of each of the two wavelengths is measured and the difference used to estimate oxygen saturation of a person's blood and changes in blood volume in the skin. A photoplethysmogram (PPG) can then be obtained using the pulse oximeter sensor or with an optical sensor using a single light source. The PPG can be used to measure blood flow and heart rate. An electroencephelogram (EEG) can be monitored using electrodes attached to the scalp and measures voltages generated by brain activity.

The converter assembly 14 converts the electrical signals generated by the sensor assembly 12 to a frequency modulated ultrasonic signal that can be received by a computing device 16. In the embodiment shown in FIG. 5, the converter assembly 14 includes a converter 23 and an ultrasonic transmitter 24 for outputting frequency modulated ultrasonic signals having a carrier frequency in a range of from, for example, about 18 kHz to about 24 kHz. Nonlimiting examples of suitable ultrasonic transmitters 24 include, but are not limited to, miniature speakers, piezoelectric buzzers, and the like. The ultrasonic signals can be received by, for example, a microphone 25 in a computing device 16 such as a smartphone 30, personal digital assistant (PDA), tablet personal computer, pocket personal computer, notebook computer, desktop computer, server computer, and the like.

Prior art devices have used frequency modulated physiological signals to communicate between acquisition hardware and a computing device. The signals have a carrier frequency within the audible range such as the traditional 19 kHz FM frequency used to transmit ECG signals. However, it has been discovered that by using ultrasonic frequencies as the carrier, such as frequencies in the range of from about 18 kHz to about 24 kHz, and even 20 kHz to 24 kHz, the acoustic communication between the acquisition electronics 11 of the personal monitoring device 10, and a computing device 16 such as a smartphone is virtually silent and far more noise-immune than the traditional 1.9 kHz FM ECG frequency. In fact, measurements of the audio signal power in the ultrasonic range determined that carrier frequencies of 17 kHz and higher provide communication that is immune to ambient and voice "noise" contamination. By using an ultrasonic carrier frequency, in even the "noisiest" environment, we create both a noise-free and a silent communication between the acquisition electronics 11 and the computing device 16 such as a smartphone 30, notebook computer, or the like.

Figure 7A:
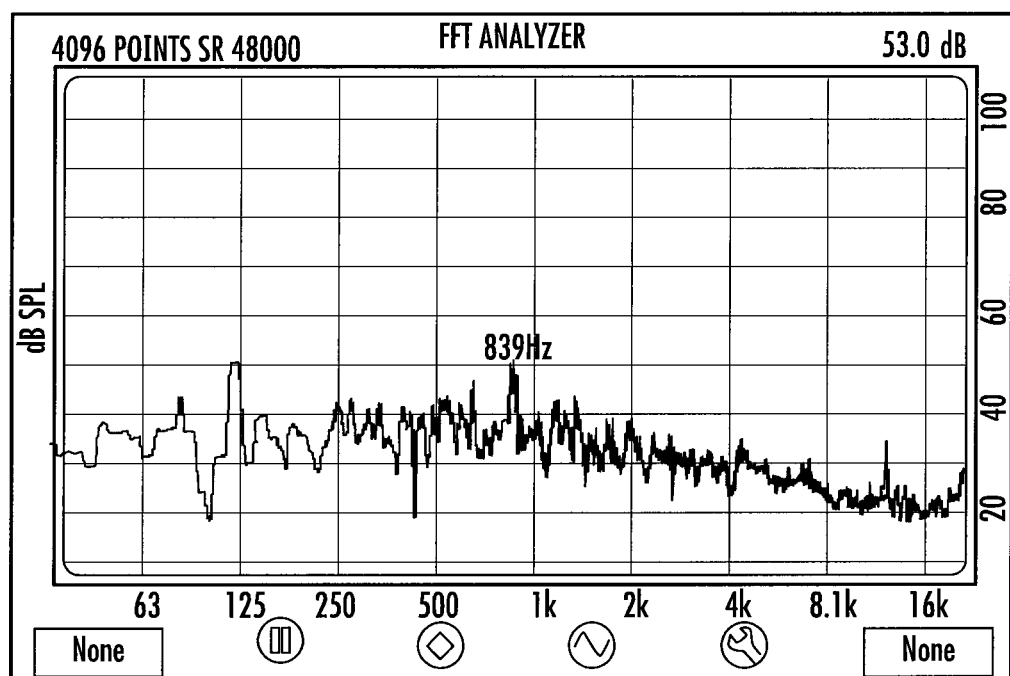
FIG. 7A is a spectrogram of the noise in a quiet office environment.
Figure 7B:
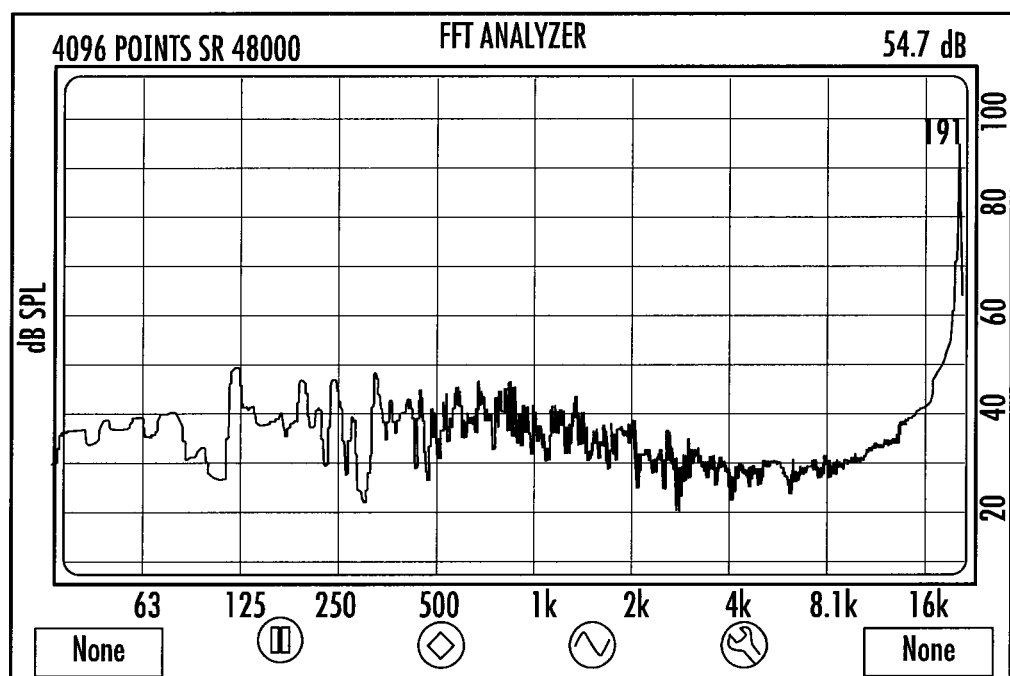
FIG. 7B is a spectrogram of a modulated ultrasonic signal from an ECG monitoring device embodied in the present invention.

For example, FIG. 7A shows a spectrogram of the sound in a quiet office environment. As can be seen, the ambient noise is about 35 db at 2 kHz. FIG. 7B shows a spectrogram of the ultrasonic modulated ECG signal in the same quiet office environment. It should be noted that the ambient noise at 19 kHz is only 20 db (the slight upturn is artifact) giving at least a 15 db advantage for a 19 kHz ultrasonic signal compared to a standard 2 kHz signal. This is a significant improvement on the signal to noise ratio (SNR) which improves even more in noisy environments such as the street, shopping mall or a noisy home. Synergistically, the volume of the signal can be further increased at the ultrasonic frequencies, without concern for "listeners" present, because they cannot hear it.

In one embodiment, the personal monitoring device 10 is an ECG device 10' and includes an electrode assembly 18 configured to sense heart-related signals upon contact with a user's skin, and to convert the sensed heart-related signals to an ECG electric signal. As discussed in detail hereinafter, the ECG device 10' transmits an ultrasonic frequency modulated ECG signal to a computing device 16 such as, for example, a smartphone 30. Software running on the computer 16 or smartphone 30 digitizes and processes the audio in real-time, where the frequency modulated ECG signal is demodulated. The ECG can be further processed using algorithms to calculate heart rate and identify arrhythmias. The ECG, heart rate, and rhythm information can be displayed on the computer 16 or smartphone 30, stored locally for later retrieval, and or transmitted in real-time to a web server 52 via a 2G/3G/4G, WiFi or other Internet connection. In addition to the display and local processing of the ECG data, the computer 16 or smartphone 30 can transmit, in real-time, the ECG, heart rate and rhythm data via a secure web connection for viewing, storage and further analysis via a web browser interface (using the 2G/3G/4G or WiFi connectivity of, for example, the smartphone 30). Server software provides for storage, further processing, real-time or retrospective display and formulation of a PDF ECG rhythm strip document and or other reports and formats for printing remotely or locally.

In another embodiment, the converter assembly 14 of ECG device 10' is integrated with, and electrically connected to the electrode assembly 18 and is configured to convert the electric ECG signal generated by electrode assembly 18 to a frequency modulated ECG ultrasonic signal having a carrier frequency in the range of from about 18 kHz to about 24 kHz. It is sometimes desirable to utilize a carrier frequency in the 20 kHz to 24 kHz range. The ultrasonic range creates both a lower noise and a silent communication between the acquisition electronics 11 and the computing device 16 such as the smartphone 30, notebook, and the like.

Figure 8A:
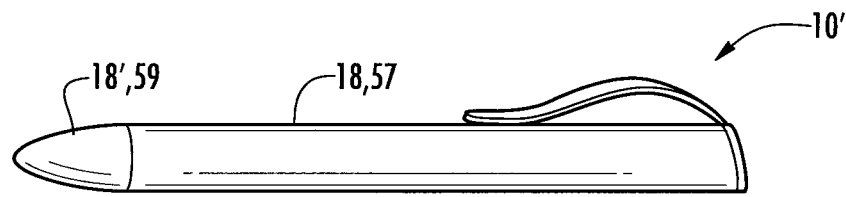
FIG. 8A is a schematic representation of an embodiment of a personal monitoring device of the present invention having a tubular shape.

The ECG device 10' can be configured in any way consistent with its function, i.e., it should include electrodes available to make contact with a user's skin on the hands, chest or other parts of the body, for obtaining the user's ECG, and means for transmitting the ECG using ultrasound to a receiving device. For example, a hand held ECG device 10' can be shaped like a credit card as in FIG. 5 with two electrodes on the bottom surface, or the ECG device 10' can be shaped like a flash light or pen as in FIG. 8A having one electrode 18 on the cylindrical surface 57 touching a holder's hand, and the other electrode 18' is on an end 59 contacting the chest, hand or other body part when in use.

Figure 8B:
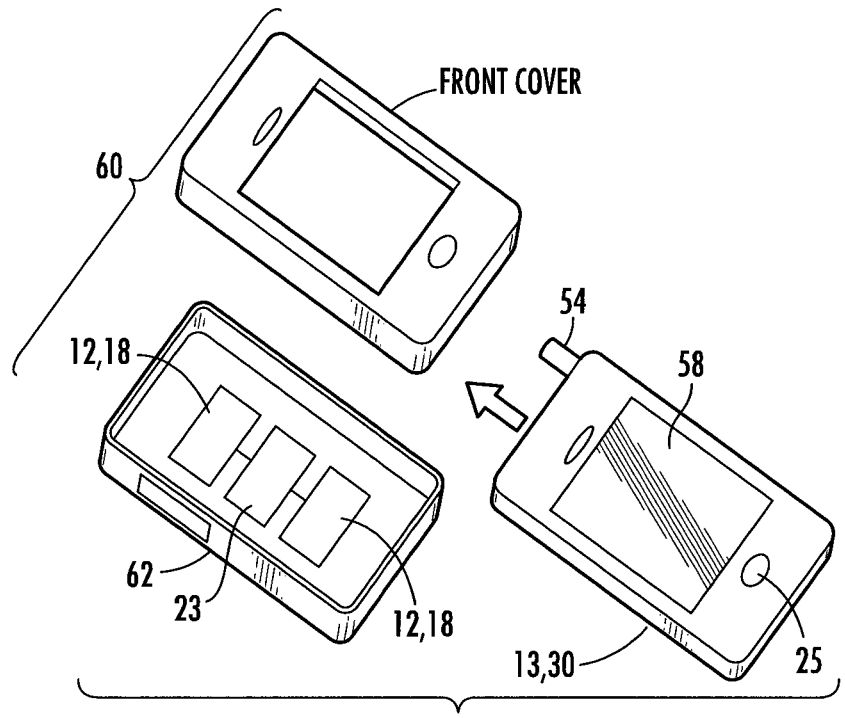
FIG. 8B is a schematic representation of another embodiment of a personal monitoring device of the present invention usable as a smartphone protective case.
Figure 8C:
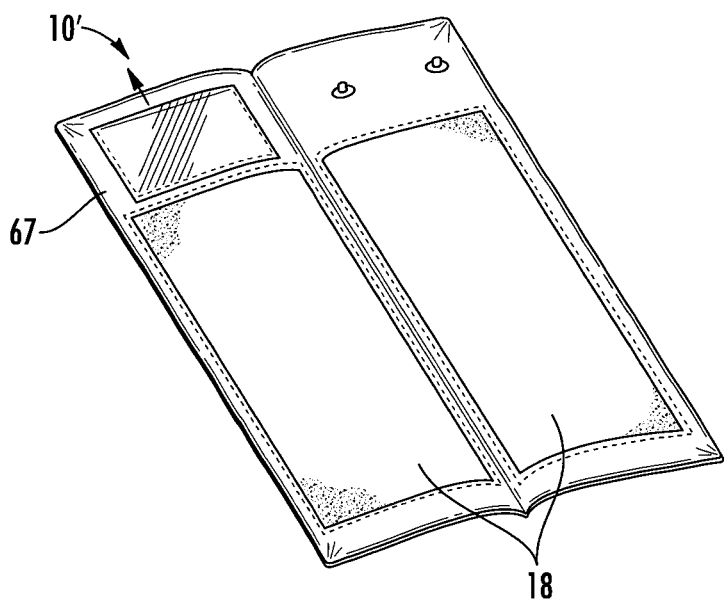
FIG. 8C is a schematic representation of an embodiment of a personal monitoring device of the present invention usable as a pad.

In another configuration, the ECO device 10' is usable as a smartphone protective case 60 as shown in FIG. 8B. One example configuration utilizes a "slip-on" protective ease 60 for an iPhone® or other smartphone 30, the protective case 60 including an integrated ECG electrode assembly 18 and acquisition electronics 11 (2, 3 or 4 electrodes for generating a single lead of ECG data). The ECG electrodes are located on the side 62 of the case 60 opposite of the display screen 58. The smartphone 30, in its ECG-adapted protective case 60, can be held in both hands (generating a lead one, Left Arm minus Right Arm) or can be placed on a person's chest to generate a modified chest lead. The ECG is measured by the acquisition electronics 11 and converted into a frequency modulated ultrasonic signal. Nonlimiting example of suitable carrier or center frequencies include from about 18 kHz to about 24 kHz, or in some embodiments from about 20 kHz to 24 kHz. The frequency modulated ultrasonic signal is output by a miniature speaker 64 or a piezoelectric buzzer 66.

Figure 9A:
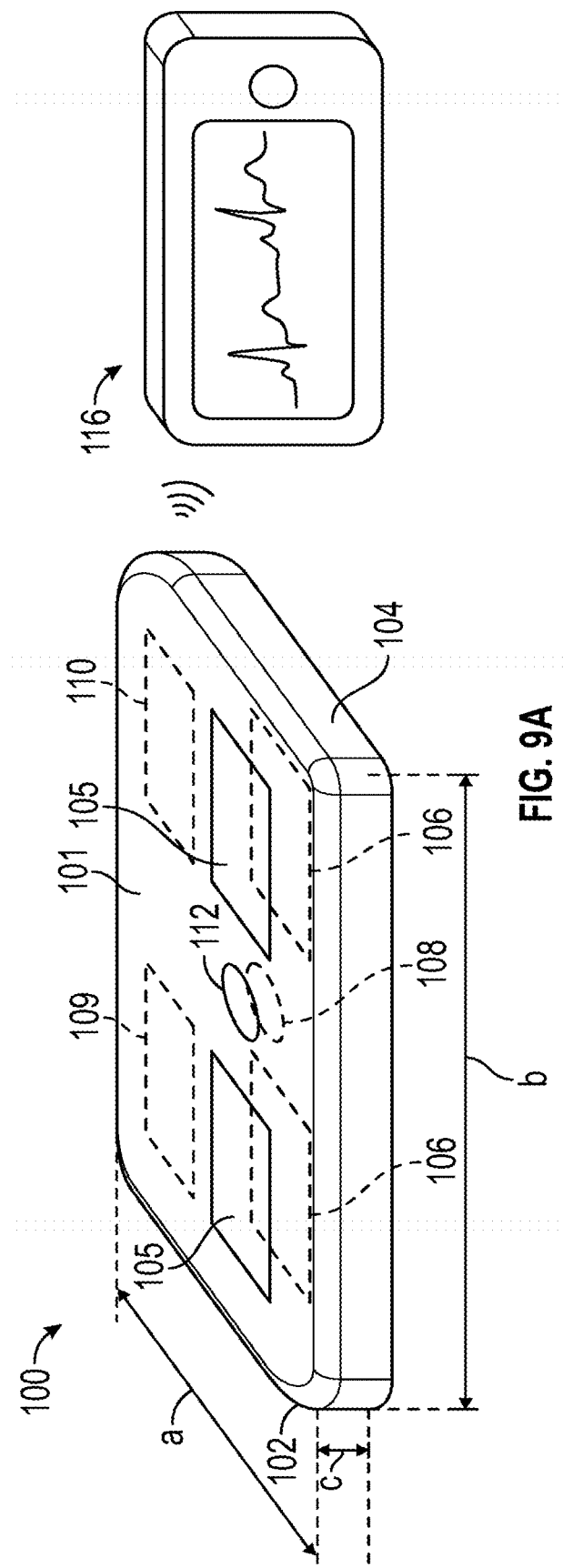
FIG. 9A is a perspective view of one embodiment of the present invention with a credit card form factor.

FIG. 9A shows another embodiment of a credit card like monitoring device 100 ("credit card sensor"), similar to that depicted as 10' in FIG. 5A, for remote or mobile acquisition of ECG data. Some embodiments may have a similar form as a financial bank or credit card, which may have a thickness of approximately 0.75 mm, and may be flexible and made of a plastic or polymer, such as polyvinyl chloride acetate (PVCA). Some embodiments of the credit card sensor have a thickness between 0.65 mm to 0.85 mm, and some between 0.70-0.78 mm. Some embodiments of the credit card sensor may have a range of bending stiffness, and some may meet the standards outlined by ISO 7810 ID-1 format. Embodiments of the credit card like senor may have a bending stiffness or flexibility permitting a user to place it in a purse or wallet in a similar manner to how a normal credit card is stored and carried.

Figure 9B:
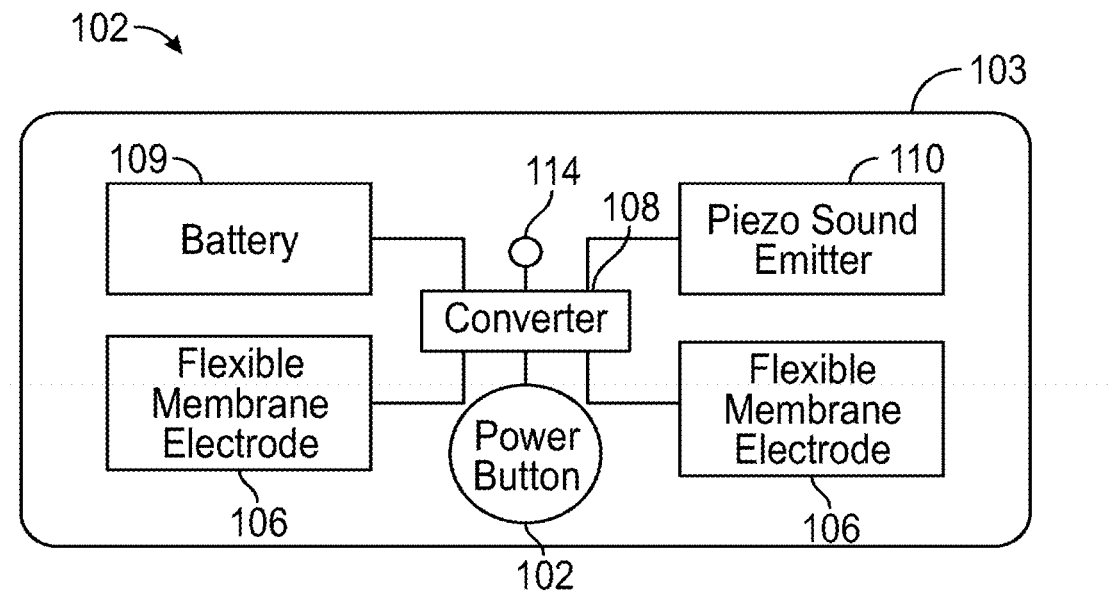
FIG. 9B depicts the underside of the upper layer of the embodiment of the present invention shown in FIG. 9A.
Figure 9C:
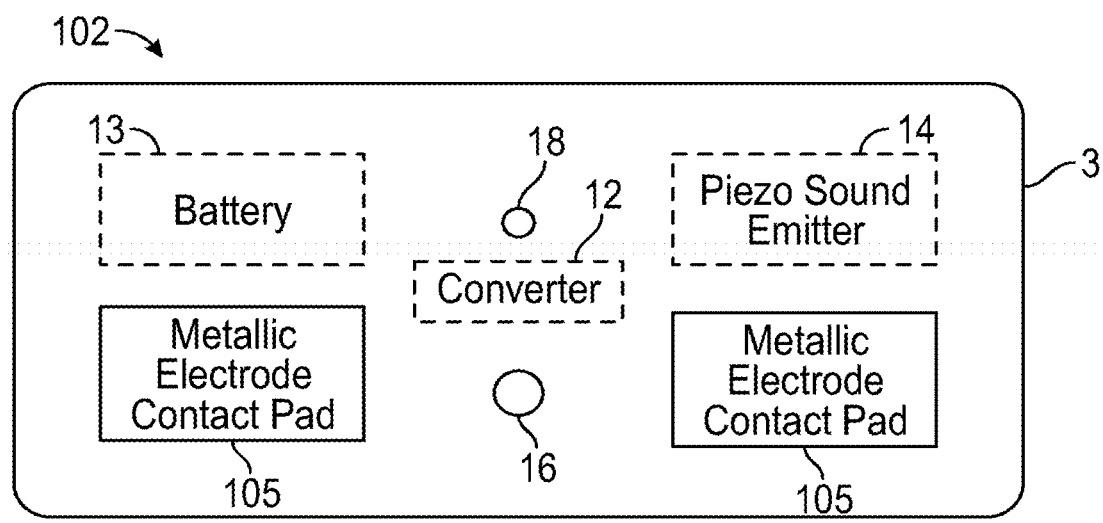
FIG. 9C depicts the topside of the upper layer of the embodiment of the present invention shown in FIG. 9A.

Referring to FIG. 9A, a perspective view of an embodiment of credit card sensor 100 is depicted. Credit card sensor 100 has a sandwich structure with upper layer 102 and lower layer 104, width a, length b and thickness c. FIG. 9B shows underside 103 of upper layer 102. Underside 103 has flexible membrane electrodes 106, one on each side of credit card sensor 100, converter 108, battery 109, piezo ultrasonic sound emitter 110, power button 112, and LED indicator 114. Battery 109 powers converter 108, which may be a printed circuit board with firmware installed thereon. FIG. 9C depicts topside 101 of upper layer 102. Topside 101 has exposed touch pads 105 that are in electrical contact with flexible membrane electrodes 106.

As described herein, a user contacts touch pads 105 (e.g., left and right fingers) that sense an electric signal for a Lead 1 ECG. Converter 108 converts the electrical signals generated from the touch pads 105 to a frequency modulated signal, for example an ultrasonic signal or Bluetooth signal (further described below), that can be received by a computing device 116. In the embodiment shown in FIGS. 9A-9C. The converter assembly includes a converter 108 and an ultrasonic transmitter 110 for outputting frequency modulated ultrasonic signals having a carrier frequency in a range of from, for example, about 18 kHz to about 24 kHz. The ultrasonic signals can be received by, for example, a microphone in computing device 116 such as a smartphone (as shown), personal digital assistant (PDA), tablet personal computer, pocket personal computer, notebook computer, desktop computer, server computer, smart watch or wearable, and the like. Computing device 116 has a microprocessor/CPU (not shown) that may do one or more of the following: acquire, digitize, demodulate, process and then display ECG data in real-time.

In an alternative embodiment, credit card sensor 100 may have a display (not shown) allowing near real time display of a user's ECG. In this embodiment, for example, credit card sensor 100 may include a receiver (not shown), which may be included with converter 108, that receives the processed ECG signal from the computing device and displays it on a display (not shown) on the credit card sensor 100. Alternatively, credit card sensor 100 may include a processor (not shown), which may be included with converter 108 having the ability to process and display the signals from touch pads 105 in a similar manner as the CPU of computing device 116. In this embodiment, all connections may be hard wired or wireless. Credit card sensor 100 may include memory (not shown), which may be part of or separate from converter 108, or the processor may include firmware (not shown), where the memory or firmware may include instructions for causing the processor to process the sensed heart-signals (e.g.. ECG signals etc.) from a user contacting the touch pads 105 and displaying the heart-signals on a display (not shown) located on an exterior surface of credit card sensor 100. Transmitter 110 may be used to transmit the processed signal to a computing device, where a medical professional may view the recording. Alternatively, computing device, once in receipt of the data, may send the data to a medical professional using well know communications and data transfer technologies.

Figure 10:
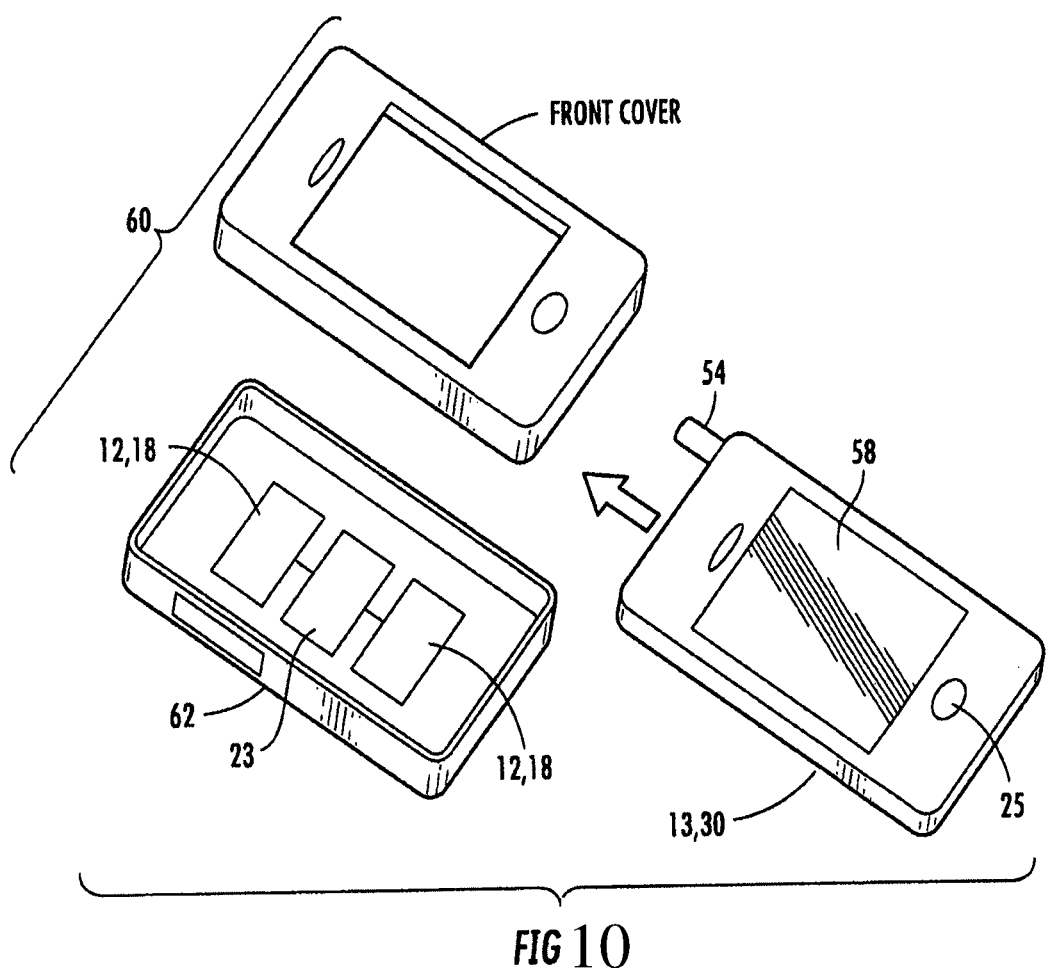
FIG. 10 is a perspective view of a personal monitoring device in accordance with one embodiment of the present invention.

In yet another embodiment, shown in FIGS. 10 (formerly 7 of '042) and 11 (formerly 8 of '042), convener assembly 108 includes a wireless radio transmitter 37 configured to convert and transmit the electrical signals generated by the sensor assembly 12 using a headset profile (HSP) of the Bluetooth® wireless communications standard is defined by the Bluetooth Special Interest Group (SIG) and available at URL address www.bluetooth.org. The electrical signals generated by the sensor assembly 12 are converted and transmitted using a Bluetooth® transceiver 34 and antenna 36 and communicated to the computing device 13, preferably a smartphone 30 or smart watch, according to instructions provided by a headset controller 38. Economy, as well as isolation and convenience, are provided by using a commercially available headset controller 38. Bluetooth® transceiver 34, and antenna 36, powered by a headset battery 40, wherein the electronics are commercially configured and mass-produced for communicating with computing devices 13 such as smartphones 30.

Computing device electronics 42 typically include a controller 44, a Bluetooth® transceiver 46 and antenna 48 for receiving input from a wireless Bluetooth® device. Most computing devices, and all smartphones and most wearables, include a memory 56, a display screen 58, and a transceiver 50 for transmitting receiving information signals to from a base station or web server 52 via a cellular antenna 54, or WiFi connection. Thus, the computing device electronics 42 can be used to store information from the personal monitoring device 10 in memory 56, and/or transmit the information to the base station 52 or a specific communication address via wireless communication technology well understood by those skilled in the art.

Figure 11:
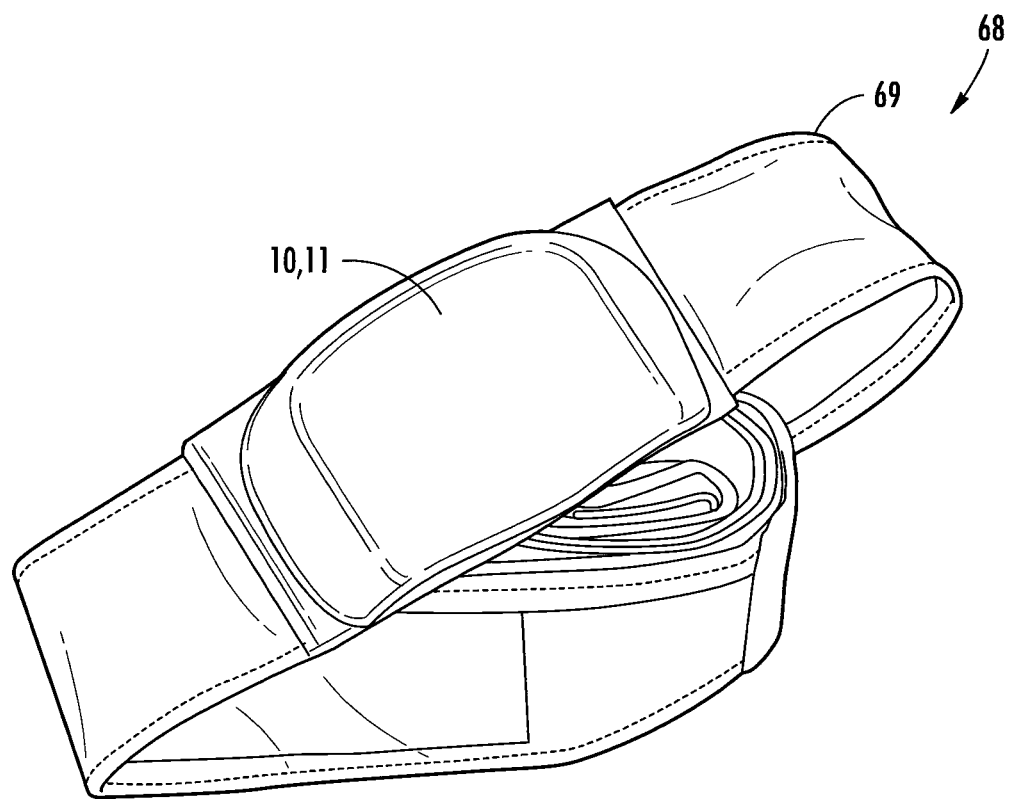
FIG. 11 is a schematic representation of an embodiment of an ECG device of the present invention included positioned within a chest strap.

In yet another embodiment, shown schematically in FIG. 11, the ECG device 10' is usable as a chest strap device 68 like a fitness heart rate monitor. The chest strap 69 with integrated ECG electrode assembly 18 and acquisition electronics 11 "pod" generate the frequency modulated ultrasonic ECG signal and send it to a computing device 16 such as the smartphone 30.

In any of the configurations, the computing device 16, such as smartphone 30, utilizes its built-in microphone 25 and CPU to acquire, digitize, demodulate, process and then display the ECG data in real-time. Also, the computing device 16, smartphone 30 or smart watch can calculate a real-time heart rate measurement and determine a cardiac rhythm diagnosis like atrial fibrillation. The computing device 16 or smartphone 30 can utilize its 2G, 3G, 4G, Bluetooth® and WiFi connectivity to transmit the ECG and other data to a secure web server 52 for real-time distant display, storage and analysis. Also, the ECG data can be stored locally on the smartphone 30 for later review or transmission.

Software on the smartphone 30 can also combine data and signals from other sensors built into the smartphone 30 such as a GPS and accelerometer. Further processing of this data provides additional information related to the user, such as speed, location, distance, steps, cadence, body position, fail detection and energy expenditure. The raw signals from the sensors and derived information can be displayed and stored locally on the smartphone 30, as well as being transmitted to the web server 52 over an internet connection. Software on the web server 52 provides a web browser interface for real-time or retrospective display of the signals and information received from the smartphone 30, and also includes further analysis and reporting.

Figure 12:
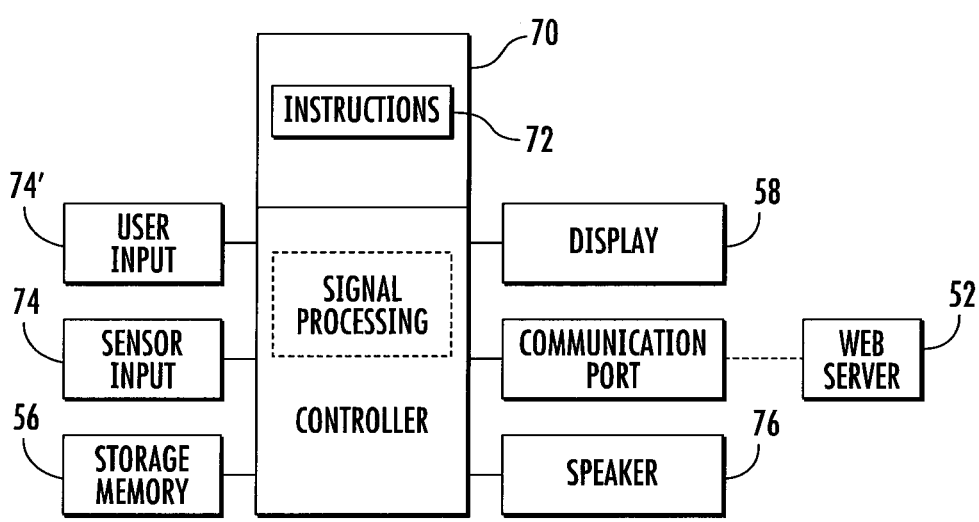
FIG. 12 is a schematic representation of a computer-readable storage medium embodiment of the present invention.

Referring now to FIG. 12, a computer-readable storage medium 56 stores a set of instructions 72, wherein the instructions 72 are capable of being executed by one or more computing devices 16. Nonlimiting examples of suitable computing devices 16 include smartphones 30, personal digital assistants (PDAs), tablet personal computers, pocket personal computers, notebook computers, desktop computers, and server computers. When the instructions 72 are executed, the one or more computing devices 16 is caused to digitize and demodulate a sensor input 74 such as an ultrasonic frequency modulated ECG signal to produce real-time demodulated digital ECG data. The instructions 72 can also cause the real-time demodulated digital ECG data to display on a display screen 58 of the computing device 16.

A common technique used for FM demodulation is based on zero crossing detection where the time interval between zero crossings is used to calculate the frequency and reconstruct the demodulated signal. In some applications simply counting the number of audio samples between zero crossings may provide sufficient accuracy for frequency estimation. Accuracy can be improved by interpolating between samples which provides a better estimate of the zero crossing point and subsequent frequency estimation. FM demodulation based on zero crossing detection is simple to implement and requires little computation compared with other techniques such as those using FFT's (fast Fourier transforms), making it particularly suitable for use in real-time applications on low power portable computing devices.

However, if the FM narrow band signal is close to the Nyquist frequency of the digitally sampled audio, the error in the zero crossing estimates become large, as there are very few samples per cycle. This severely limits the use of typical zero crossing demodulation techniques for ultrasonic carrier frequencies. An embodiment of the present disclosure provides a method to demodulate FM narrow band signals close to the Nyquist frequency, while maintaining the simplicity and efficiency of the zero crossing technique, with accurate frequency estimation.

Figure 13:
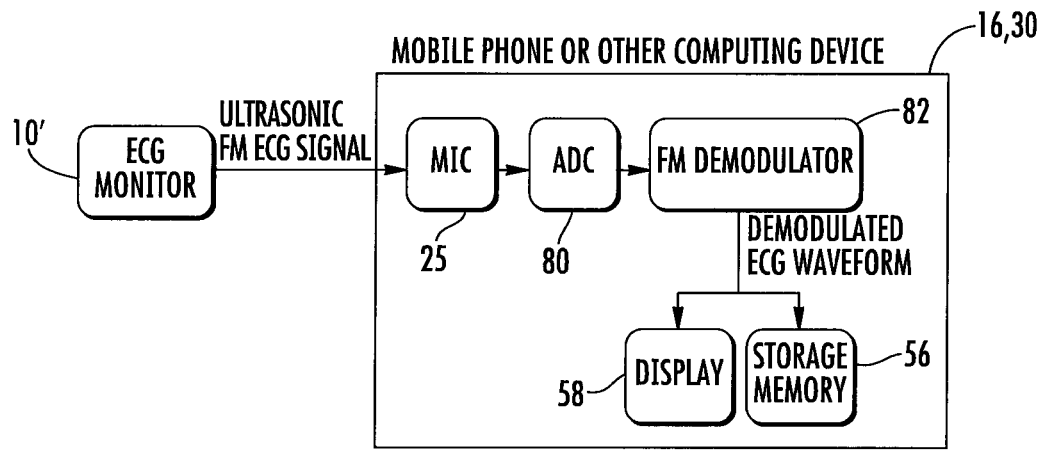
FIG. 13 is a schematic representation of an embodiment of the present invention.

Referring now to FIG. 13, an ultrasonic FM signal representing ECG signals is picked up by a microphone 25 in, for example, a mobile phone 30 or other computing device 16, and converted to an analog signal. The analog signal is continuous in time and is converted to a flow of digital values in an an a log-to-digital converter 80, demodulated in FM demodulator 82 and shown on a display 58 of the smart phone 30 or other computing device 16, or retained in storage memory 56. Since a practical analog-to-digital converter 80, commonly referred to as an ADC, cannot make an instantaneous conversion, the input value must necessarily be held constant during the time that the converter performs a conversion. The rate at which the new digital values are sampled from the analog signal is called the sampling rate or sampling frequency of the ADC. Mobile phones and other personal computing devices are typically limited to recording audio at 44 kHz. Some smart phones such as ANDROID® and IPHONE® can sample at 48 kHz.

Figure 14:
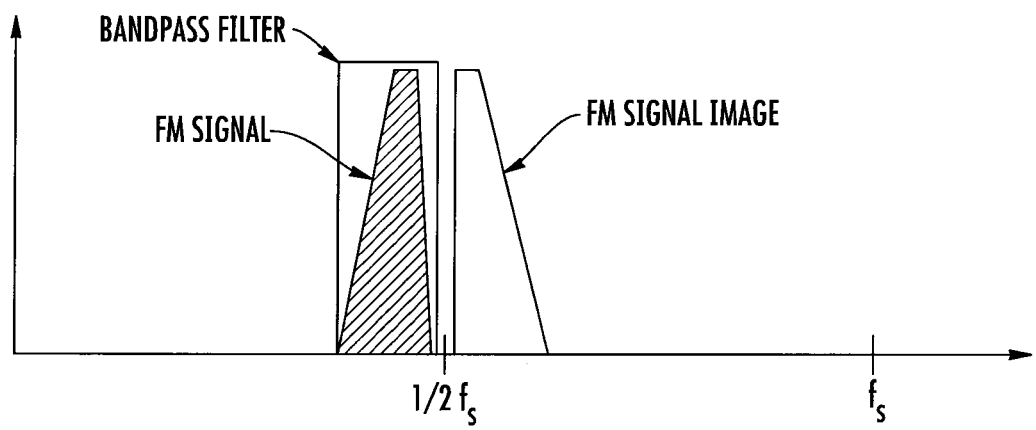
FIG. 14 is an example representation of a frequency spectrum after bandpass filtering.
Figure 15:
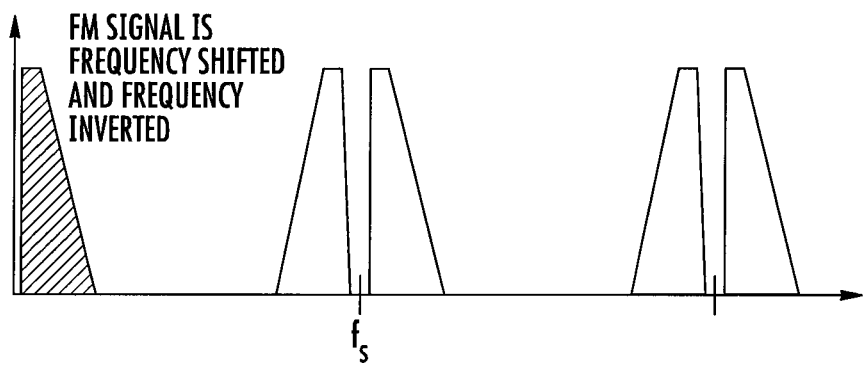
FIG. 15 is an example representation of a frequency spectrum after under-sampling at half the original sampling rate.

The digitized ultrasonic signal can then be bandpass filtered around the ultrasonic carrier frequency of the FM signal to improve signal-to-noise and reduce unwanted audio outside the passband. The filtered FM signal, as depicted in FIG. 14, is then "under-sampled" at half the sampling rate of the original audio. This results in aliasing of the FM signal that shifts and inverts the frequency spectrum to a lower frequency band. The result of the frequency spectrum being inverted by the under-sampling operation, results in the demodulated output being inverted as depicted in FIG. 15. The inversion is corrected by simply convening the final demodulated output.

With the FM signal at a lower frequency there are more audio samples per cycle and demodulation processes, such as zero crossing estimates, are significantly more accurate. For example, the zero crossing detector identifies the zero crossings where the audio signal changes sign. The accuracy of the zero crossing point is further improved by linearly interpolating between samples either side of the zero crossing. Finally, the period between zero crossings is used to calculate an estimate of the frequency and reconstruct the demodulated signal. While the above-described demodulation procedure utilizes a zero crossing estimate, it is understood that other demodulation procedures can be utilized and that the accuracy of other demodulation procedures will also benefit from the under-sampling operation.

EXAMPLE

Figure 16:
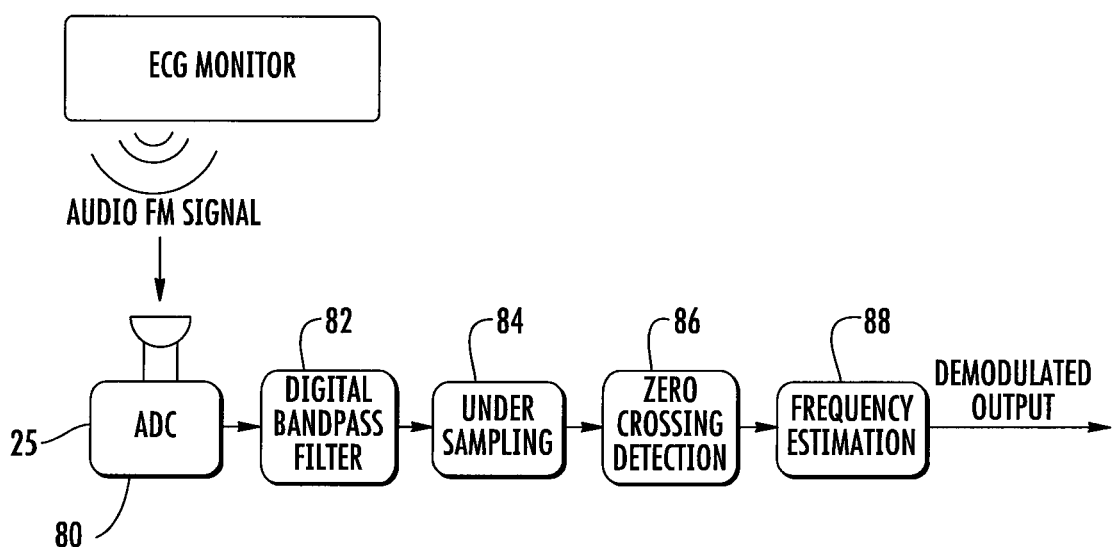
FIG. 16 illustrates a working example of a system for receiving and demodulating an ultrasonic FM ECG sound signal.

In one working example, illustrated in FIG. 16, a system used an ultrasonic KM ECG signal transmitted from a portable EGG monitor to a microphone 25 in a mobile phone 30 as well as a personal computer 16. This provided a low-cost wireless transmission solution that is compatible with most mobile phones and computers that have a microphone, without requiring any additional hardware to receive the signal.

It is desirable that the FM signal is above 18 kHz, so that it is inaudible to most people, does not interfere with music or speech, and is also less prone to audio interference. It is also desirable for the FM signal to have a narrow bandwidth to further reduce its susceptibility to audio interference. In this case the ECG monitor used an ultrasonic FM carrier of 19 kHz, modulated with an ECG at 200 Hz/mV and having a range ±5 mV. This resulted in an ultrasonic FM signal between 18 kHz and 20 kHz.

First, the audio FM signal was picked up by a microphone 25 and digitized by the ADC 80 in the mobile phone 30 at 44 kHz. The audio was then bandpass filtered in filter 82 between 18 kHz and 20 kHz to remove audio noise outside the pass band. In the next stage 84 the audio was under-sampled at 22 kHz, where only every second audio sample is used. The digital signal produced after such under-sampling results in aliasing that shifts and inverts the frequency spectrum so that it appears in the 2 kHz to 4 kHz range. A zero crossings detector 86 then identifies where the audio signal changes sign. The zero crossing point is then more accurately calculated in the frequency estimation step 88 by linearly interpolating between samples either side of the zero crossing. In this example, a frequency estimate is only required every 3.33 ms, for it demodulated output signal at 300 Hz. This is achieved by counting the number of zero crossings and measuring the period over the nearest fixed number of cycles during this period, providing a fixed 300 Hz output. The demodulated output is then inverted to correct for the frequency spectrum being inverted by the under-sampling operation. Finally the 300 Hz demodulated ECG data is passed through a 40 Hz low pass filter since the ECG bandwidth of interest is below 40 Hz. This further reduces any noise from the frequency estimates and demodulated output. The FM demodulator outputs 16 bit, 300 Hz ECG.

Sensor input 74 can also include real-time information from additional sensors as well as user input 74'. For example, in embodiments wherein the computing device 16 is a smartphone 30, the input 74 can include real-time information from a GPS and/or accelerometer in the smartphone 30 in addition to the demodulated digital ECG data. User input 74' can also include spoken voice messages entered through a microphone of the computing device 16. Instructions 72 can cause the sensor and/or user input 74 and 74' to be recorded and maintained in a storage memory 56 of the computing device 16.

In one embodiment, the set of instructions 72, when executed by the one or more computing devices 16, can further cause the one or more computing devices 16 to calculate and display in real-time, a heart rate represented by the frequency modulated ECG ultrasonic signal. In addition, demodulated digital ECG data can be processed to identify the occurrence of an arrhythmia. In such designs, the storage medium 70 can include instructions 72 to cause the computing device 16 to display a warning on a display screen 58 or emit an audible alert through the speaker 76 at the occurrence of an arrhythmia, Instructions 72 can cause the computing device 16 to store the demodulated digital ECG data in a memory 56 of the one or more computing devices 16 for later retrieval. The set of instructions 72 can further cause the one or more computing devices 16 to retrieve and transmit, upon demand, the stored demodulated digital ECG data to a web server 52 via an internet connection on the computing device 16. Recorded spoken voice messages can be stored and transmitted to the web server 52, simultaneously with the demodulated digital ECG data.

In other embodiments, the instructions 72 can cause the one or more computing devices 16 to transmit the demodulated digital ECG data, and/or voice messages, to the web server 52 in real-time.

A version of the smart phone software is packaged as a software library that can be integrated with other third party software applications. This provides a simplified and standard method for third party applications to use the ECG device 10' to obtain heart rate and other derived information without having to develop their own data acquisition, demodulation, and signal processing algorithms.

A version of the software also runs on a PC and includes demodulation, processing, storage and transmission to die web server 52. The software includes the audio acquisition, demodulation, ECG analysis, and acceleration analysis modules.

Audio samples from the ADC are optionally passed through a digital band-pass filter to remove unwanted frequencies outside the modulation range. The demodulation module demodulates the frequency modulated ECG ultrasonic signal using undersampling at about one-half the frequency of the audio sample to shift the spectrum to a lower frequency range, followed by a linear approximation and zero crossings algorithm. The demodulator allows selection of different modulation parameters to match the particular ECG device. While demodulation using zero crossings and linear approximation alone works well for carrier frequencies 6 kHz and lower, above 10 kHz with 44 kHz sampling, the errors from linear approximation become large unless undersampling is used to shift the spectrum.

The algorithm then looks at the sign of incoming data. When the sign changes it draws a straight line between the two points and interpolates the zero value. It uses this to determine the average frequency over a 3.333 ms interval, which provides ECG data at the output sampling rate of 300 Hz.

The ECG analysis module includes algorithms that process the ECG to detect and classify boats, and provides a heart rate estimate. Beat-to-beat heart rate is calculated from the interval between boats and a more robust measurement of heart rate is calculated using median filtering of the RR intervals.

The acceleration analysis module includes algorithms that process signals from the built-in 3 axis accelerometer sensor in the smartphone 30, to derive an estimate of a person's energy expenditure, steps, cadence, and body position and to detect falls.

From the above descriptions, it is clear that the presently disclosed and claimed inventive concept(s) are well-adapted to carry out the objects and to attain the advantages mentioned herein, as well as those inherent in the presently disclosed and claimed inventive concept(s). While the presented embodiments have been described for purposes of this disclosure, it will be understood that numerous changes may be made which will readily suggest themselves to those skilled in the art and which are accomplished within the spirit of the presently disclosed and claimed inventive concept(s).

What is claimed is:

1. A mobile ECG sensor comprising:
   an electrode assembly comprising electrodes, wherein the electrode assembly senses heart-related signals when in contact with a user's skin, and produces electrical signals representing the sensed heart-related signals;
   a converter assembly electrically connected to the electrode assembly, configured to convert the electrical signals to a modulated signal, wherein the modulated signal carries the electrical signals representing the sensed heart-related signals;

a transmitter that transmits the modulated signal wirelessly to a computing device; and a housing containing the electrode assembly, the converter assembly, and the transmitter.

2. The mobile ECG sensor according to claim 1, wherein the housing is a credit card form factor.

3. The mobile ECG sensor according to claim 2, wherein the electrode assembly comprises at least two electrode pads positioned on an exterior surface of the credit card form factor.

4. The mobile ECG sensor according to claim 3, wherein the credit card form factor comprises a top part with a top surface and an underside, and a bottom part with a topside and a bottom surface, wherein the underside of the top part is affixed to the topside of the bottom part, wherein the electrode assembly further comprises at least two conductive flexible membranes electrically connected to the at least two electrode pads and electrically connected to the converter, and wherein the at least two electrode pads are positioned on the top surface of the top part, and the at least two conductive flexible membranes are positioned between the underside of the top part and the topside of the bottom part.

5. The mobile ECG sensor according to claim 4, wherein the at least two conductive flexible membranes are in contact with the at least two electrode pads.

6. The mobile ECG sensor according to claim 4, wherein the modulated signal is a frequency modulated signal, and wherein the transmitter outputs the frequency modulated signal having a carrier frequency in the range of from about 6 kHz to about 20 kHz.

7. The mobile ECG device according to claim 4, wherein the modulated signal is in accordance with Bluetooth® protocol.

8. The mobile ECG device according to claim 4, wherein the modulated signal is in accordance with a headset profile of the Bluetooth wireless communication standard.

9. The mobile ECG sensor according to claim 1, wherein the housing is a mobile phone case form factor, and wherein the electrodes are positioned on an exterior surface of the mobile phone case form factor.

10. A mobile ECG sensor comprising:
a credit card form factor, wherein the credit card form factor houses:
an electrode assembly comprising electrodes positioned on an exterior surface of the credit card form factor, wherein the electrode assembly senses heart-related signals when in contact with a user's skin, and produces electrical signals representing the sensed heart-related signals;
a converter assembly electrically connected to the electrode assembly, the converter assembly comprising a processor;
a display electrically connected to the converter assembly, the display positioned on the exterior surface of the credit card form factor; and
a memory comprising instructions to cause the processor to process the sensed heart-related signals and display the heart-related signals on the display.

11. The mobile ECG sensor according to claim 10, wherein the heart-related signals comprises ECG signals.

12. The mobile ECG sensor according to claim 10, wherein the heart-related signals comprises heart rate signals.

13. The mobile ECG sensor according to claim 10, further comprising a transmitter electrically connected to the processor and housed in the credit card form factor, wherein the transmitter is capable of transmitting the processed heart-related signal wirelessly.

* * * * *

Disclaimer

11,103,175 B2 - David E. Albert, Oklahoma City, OK (US); Simon Prakash, Los Gatos, CA (US); Bruce Satchwell, Gold Coast (AU); Jonathan Beck, Mountain View, CA (US). MOBILE ECG SENSOR APPARATUS. Patent dated August 31, 2021. Disclaimer filed October 11, 2022, by the assignee, AliveCor, Inc.

I hereby disclaim the following complete claims 1-13 of said patent.

*(Official Gazette, March 14, 2023)*